US012616522B2

(12) United States Patent
Widmer et al.

(10) Patent No.: US 12,616,522 B2
(45) Date of Patent: May 5, 2026

(54) METHOD FOR DETERMINING THE SCREW TRAJECTORY OF A PEDICLE BONE SCREW

(71) Applicant: 25SEGMENTS AG, Zürich (CH)

(72) Inventors: Jonas Widmer, Zürich (CH);
Sebastiano Caprara, Zürich (CH);
Mazda Farshad, Zumikon (CH)

(73) Assignee: 25SEGMENTS AG, Zürich (CH)

( * ) Notice: Subject to any disclaimer, the term of this patent is extended or adjusted under 35 U.S.C. 154(b) by 358 days.

(21) Appl. No.: 18/266,696

(22) PCT Filed: Dec. 13, 2021

(86) PCT No.: PCT/EP2021/085554
§ 371 (c)(1),
(2) Date: Jun. 12, 2023

(87) PCT Pub. No.: WO2022/128956
PCT Pub. Date: Jun. 23, 2022

(65) Prior Publication Data
US 2024/0299095 A1     Sep. 12, 2024

(30) Foreign Application Priority Data

Dec. 14, 2020     (EP) ..................................... 20213746

(51) Int. Cl.
*A61B 34/10*          (2016.01)
*G06T 7/246*          (2017.01)
*G06T 19/20*          (2011.01)

(52) U.S. Cl.
CPC .............. *A61B 34/10* (2016.02); *G06T 7/251* (2017.01); *G06T 19/20* (2013.01);
(Continued)

(58) Field of Classification Search
None
See application file for complete search history.

(56) References Cited

U.S. PATENT DOCUMENTS

| | | | |
|---|---|---|---|
| 2004/0240715 A1 | 12/2004 | Wicker et al. | |
| 2005/0192575 A1 | 9/2005 | Pacheco | |

(Continued)

FOREIGN PATENT DOCUMENTS

| | | | |
|---|---|---|---|
| CN | 109069166 A | 12/2018 | |
| CN | 109199604 A | 1/2019 | |

(Continued)

OTHER PUBLICATIONS

Jun. 29, 2023—(PCT/EP) International Preliminary Report on Patentability & Written Opinion—App 2021/085554.

(Continued)

*Primary Examiner* — Kyle Zhai
(74) *Attorney, Agent, or Firm* — Banner & Witcoff, Ltd.

(57)     ABSTRACT

A method for determining the screw trajectory of a pedicle bone screw comprises: obtaining a CT image of the target bone area intended to receive the pedicle bone screw, establishing an individualized three-dimensional geometric model of the target bone area based on the CT image, accessing a database comprising a three-dimensional bone area model; wherein the bone area model comprises a bone screw insertion surface and a pedicle traversing surface for each pedicle, morphing the bone area model to the geometric model of the target bone area generating a morphed vertebra model with a bone screw insertion surface and the pedicle traversing surface, calculating a maximum of bone density when the bone material is replaced by a bone screw for a bone screw in the morphed vertebra model of the target bone, and outputting the space vector of the screw trajectory for the bone screw together with the length and diameter of the bone screw in the morphed vertebra model of the target bone.

20 Claims, 11 Drawing Sheets

(52) U.S. Cl.
CPC ... *A61B 2034/104* (2016.02); *A61B 2034/105* (2016.02); *A61B 2034/107* (2016.02); *G06T 2207/10081* (2013.01); *G06T 2207/30012* (2013.01); *G06T 2207/30241* (2013.01); *G06T 2210/41* (2013.01); *G06T 2210/44* (2013.01); *G06T 2219/2021* (2013.01)

(56) References Cited

U.S. PATENT DOCUMENTS

| | | | |
|---|---|---|---|
| 2010/0106010 A1 | 4/2010 | Rubner et al. | |
| 2017/0112575 A1 | 4/2017 | Li et al. | |
| 2018/0250075 A1 | 9/2018 | Cho | |
| 2019/0029757 A1* | 1/2019 | Roh | G16H 20/40 |
| 2019/0133690 A1* | 5/2019 | Buerger | A61B 34/10 |

FOREIGN PATENT DOCUMENTS

| | | | | |
|---|---|---|---|---|
| CN | 110946652 A | 4/2020 | | |
| EP | 3120797 A2 | 1/2017 | | |
| EP | 3566669 A1 | 11/2019 | | |
| EP | 3932357 A1 * | 1/2022 | | A61B 34/10 |
| WO | 2005081863 A2 | 9/2005 | | |
| WO | 2008038284 A2 | 4/2008 | | |
| WO | 2016102025 A1 | 6/2016 | | |
| WO | 2017186799 A1 | 11/2017 | | |

OTHER PUBLICATIONS

Apr. 8, 2022—(PCT/EP) International Search Report and Written Opinion—App 2021/085554.
Jul. 28, 2025—CN First Office Action—App No. 202180083898.1.

* cited by examiner

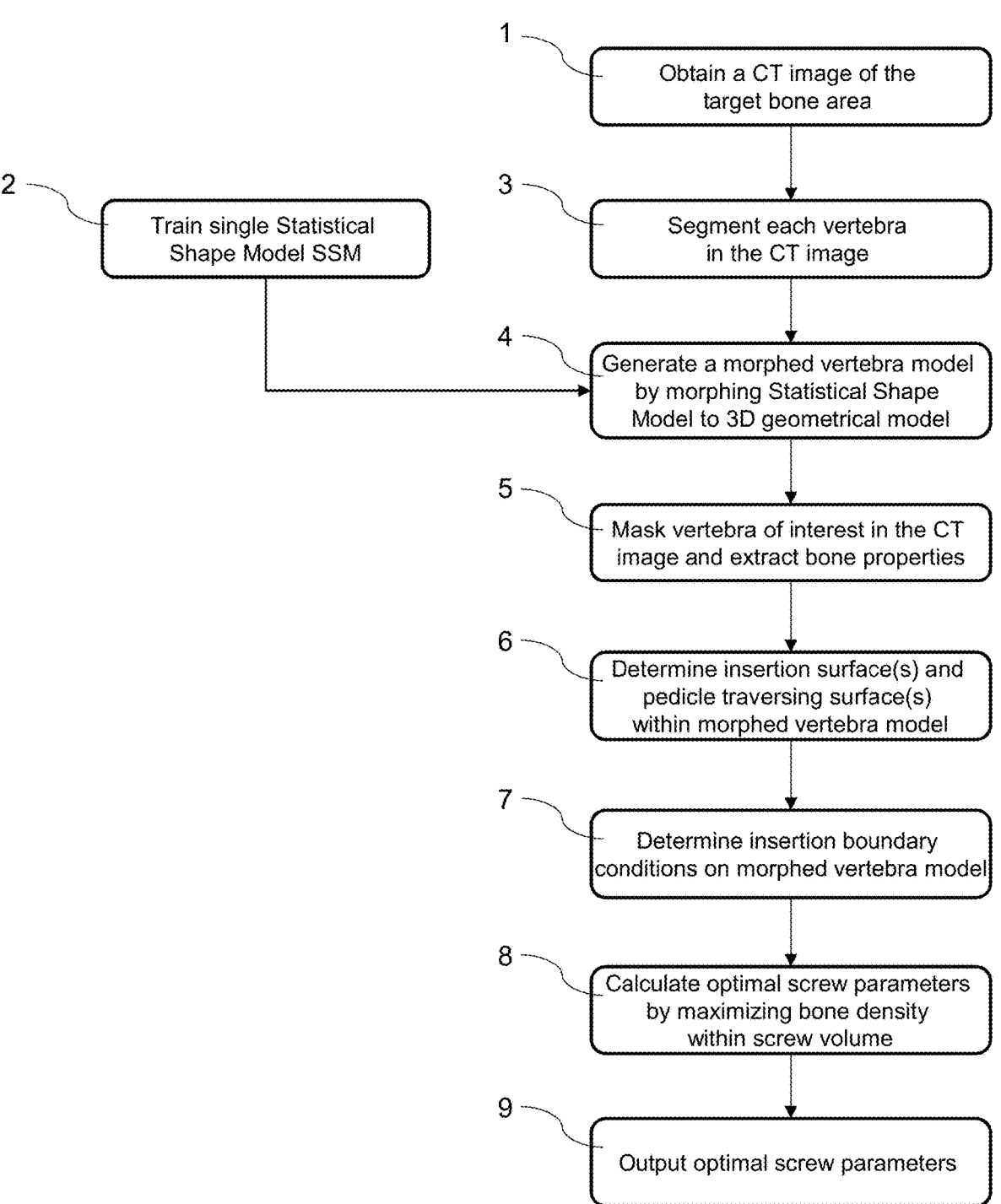

1 — Obtain a CT image of the target bone area

2 — Train single Statistical Shape Model SSM

3 — Segment each vertebra in the CT image

4 — Generate a morphed vertebra model by morphing Statistical Shape Model to 3D geometrical model 5 — Mask vertebra of interest in the CT image and extract bone properties 6 — Determine insertion surface(s) and pedicle traversing surface(s) within morphed vertebra model 7 — Determine insertion boundary conditions on morphed vertebra model 8 — Calculate optimal screw parameters by maximizing bone density within screw volume 9 — Output optimal screw parameters

Fig. 1

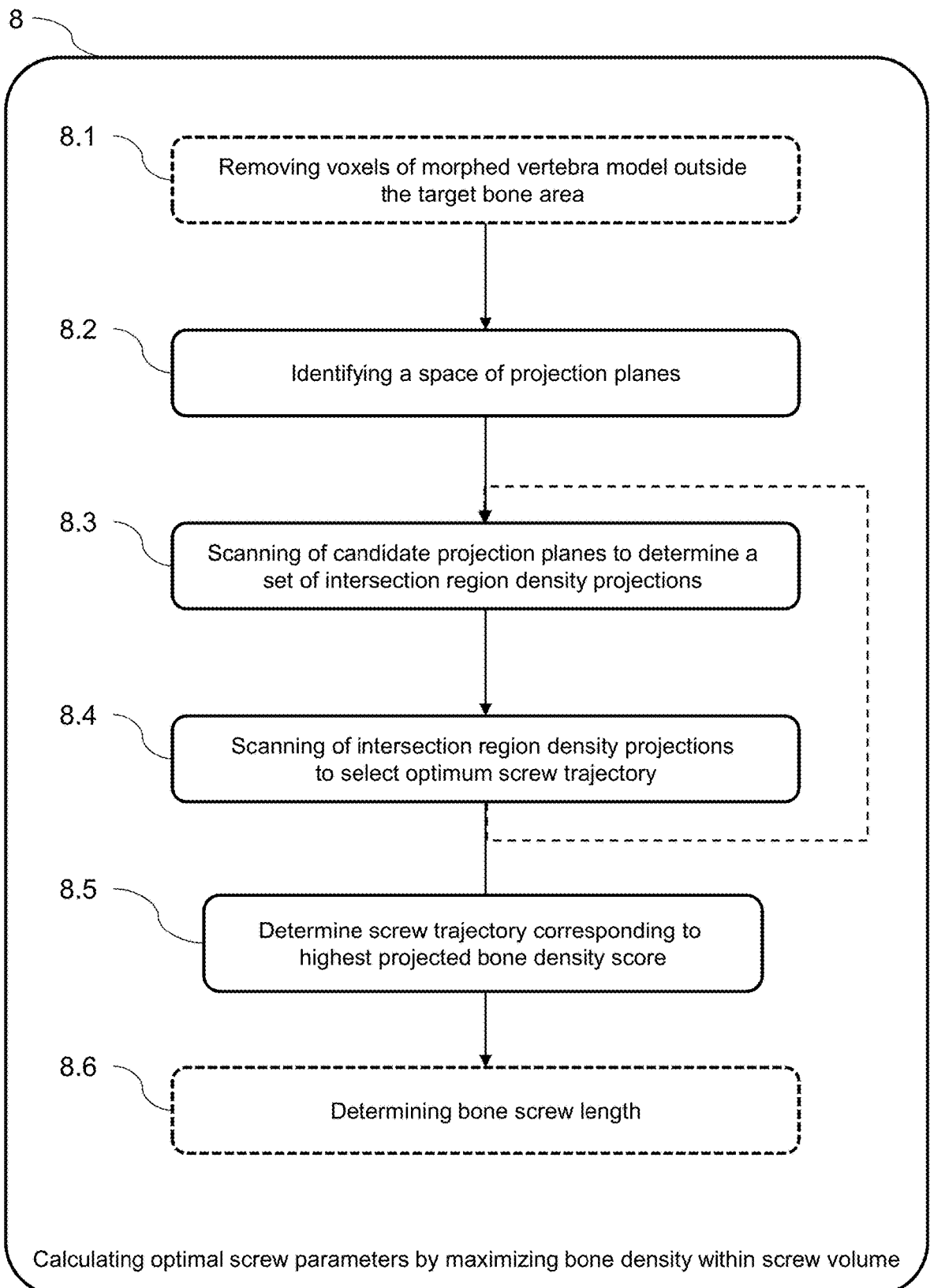

8

8.1 Removing voxels of morphed vertebra model outside the target bone area 8.2 Identifying a space of projection planes 8.3 Scanning of candidate projection planes to determine a set of intersection region density projections 8.4 Scanning of intersection region density projections to select optimum screw trajectory 8.5 Determine screw trajectory corresponding to highest projected bone density score 8.6 Determining bone screw length Calculating optimal screw parameters by maximizing bone density within screw volume

For each intersection region density projection:

For each possible screw diameter

For each possible location of screw diameter within intersection region

Calculating projected bone density score

Scanning of intersection region density projections

47

43

S

43

P1

P1

20

I1-n

10

METHOD FOR DETERMINING THE SCREW TRAJECTORY OF A PEDICLE BONE SCREW

CROSS-REFERENCE TO RELATED APPLICATIONS

The present application is a U.S. National Phase filing of International Application No. PCT/EP2021/085554, filed on Dec. 13, 2021, and claiming priority to European Patent Application No. 20213746.9 filed Dec. 14, 2020. The present application claims priority to and the benefit of all the above-identified applications, which are all incorporated by reference herein in their entireties.

TECHNICAL FIELD

The present disclosure relates to a method for determining the screw trajectory of a pedicle bone screw, a data processing system comprising means for determining the screw trajectory of a pedicle bone screw as well as a computer program product comprising instructions which, when the program is executed by a computer, cause the computer to plan the screw trajectory of a pedicle bone screw.

BACKGROUND OF THE DISCLOSURE

CN 110946652 A discloses a screw trajectory determining method of a bone screw, comprising the steps of establishing an individual three-dimensional geometric model of a target bone, and a three-dimensional bone density model containing spatial distribution information of bone density, setting bone screw parameters, and calculating the space vector of a bone screw trajectory, calculating a space helical line of bone threads as a bone screw thread curve; and placing the bone screw thread curve into the individual three-dimensional geometric model of the target bone, extracting the bone density at points of contact with bone screw threads in the individual three-dimensional geometric model of the target bone, and calculating an average value of the bone density at the contact positions; and determining a bone screw trajectory according to the bone screw parameters, the bone density and the distribution of the bone density. According to the method, by obtaining coordinates of the bone and bone screw contact positions on the three-dimensional scale, the bone density around the screw threads is determined accurately and allows determining a screw trajectory of the bone screw according to the fixation performance of the bone screw.

US 2017/112575 A1 discloses a non-transitory computer readable media embodying a program of instructions executable by machine to perform operations for pedicle screw positioning, the operations comprising: receiving image data of at least a portion of a spine; segmenting at least one vertebra of interest in the image data; determining two pedicle regions within the segmented vertebra of interest; determining one or more safe regions within the segmented vertebra of interest; generating two optimal insertion paths within the one or more safe regions, wherein the two optimal insertion paths pass through respective centres of the pedicle regions; and displaying the two optimal insertion paths for pedicle screw positioning. The method uses voxels and distances of the voxels within a segmented vertebra of interest from a nearest vertebral edge to determine the safe region for a screw to be implanted, by assigning the voxel to the safe region if the distance to such an edge being greater than a threshold distance.

US 2004/240715 A1 discloses a method for determining the placement of a pedicle screw comprising determining a trajectory for the placement of such a pedicle screw in a patient from a set of 2D images, wherein the step of determining the trajectory comprises: computing an optimum implant trajectory of the pedicle screw by determining the minimum transverse pedicle width for all of the 2D image slices that contain the vertebra under study, and determining for the vertebra under study the overall minimum transverse pedicle width of the minimum transverse pedicle for all of the 2D images slices.

CN 109199604 A discloses a pedicle screw optimal entry point positioning method based on feature vectors of a three-dimensional mesh model as input into a decision tree classification model.

SUMMARY OF THE DISCLOSURE

Based on this prior art, the present disclosure provides an alternative method to optimize screw parameters, comprising size and orientation, based on patient-specific bone properties, especially bone density of the replaced screw volume.

According to the present disclosure, this is addressed by the features of the independent claim 1. In addition, further advantageous embodiments follow from the dependent claims and the description.

In particular, this is addressed by a method for determining the screw trajectory of a pedicle bone screw comprising the following steps:

obtaining a CT image of the target bone area intended to receive the pedicle bone screw, establishing an individualized three-dimensional geometric model of the target bone area based on the CT image including bone density information, accessing a database comprising a three-dimensional bone area model; wherein the bone area model comprises a bone screw insertion surface and a pedicle traversing surface, morphing the bone area model to the geometric model of the target bone area generating a morphed vertebra model with a bone screw insertion surface and a pedicle traversing surface, calculating an optimal screw trajectory of the pedicle bone screw maximizing bone density when bone material is replaced by the pedicle bone screw in the morphed vertebra model of the target bone area, and outputting the optimal screw trajectory for the pedicle bone screw together with the length and diameter of the bone screw in the morphed vertebra model of the target bone.

The database to be accessed comprise data relating to three-dimensional bone density model with a predetermined bone screw insertion surface and a predetermined pedicle traversing surface. According to embodiments disclosed, the three-dimensional bone density model is based and trained on examined bone specimen. The morphing step then allows to automatically transfer these bone screw insertion surface and a pedicle traversing surfaces onto the 3D bone image model of the vertebra of interest.

According to embodiments disclosed, the morphing of the bone area model comprises providing a 3D pedicle traversing surface within the geometric model of the target bone. This is used to identify possible bone screw trajectories. According to embodiments disclosed, the 2D pedicle traversing surface for the pedicle traversing surface is based on the 3D pedicle traversing surface and is determined as the plane of minimum transverse pedicle width in the pedicle. The plane of minimum traverse pedicle width corresponding the plane (cross section) of the 3d pedicle traversing surface where the pedicle has the minimum width in a transverse direction.

The 3D traversing surface and the 2D traversing surface are modelled in the geometric model of the target bone area within the database and are morphed together with the other elements of the geometric model on the target bone area. This allows to start the calculation without having a direct evaluation of the areas of the vertebra of interest.

The step of morphing of the bone area model can in an alternative way comprise providing a sagittal plane within the geometric morphed vertebra model to determine the pedicle traversing surface. According to a further embodiment, the morphing of the bone area model can comprise determining the vertebral foramen within the geometric morphed vertebra model to determine the pedicle traversing surface as smallest bone material diameter on the sides of the vertebral foramen.

According to embodiments disclosed, a first threshold value as contour safety distance is provided within the determination of the 2D pedicle traversing surface for the pedicle traversing surface. Such a safety distance can be e.g. 1 or 2.5 mm and is generated as a 3D curve inside the outer edge of the pedicle and delimits the voxels used in the 3D and subsequently 2D pedicle traversing surface used in the method. Additionally, a second threshold value as length safety distance can be provided within the determination of the screw length based on a body side surface of the body of the bone area in order to not calculate a solution (i.e. a screw trajectory and the length and diameter of the pedicle bone screw) which would go beyond the other side of the body area of the vertebra.

Furthermore, the sagittal plane of the body of the intended bone area provides a third threshold value for the contour and the tip of the screw, defining a forbidden area for the screw which the screw has not to pass for any one bone screw to be introduced into the same body of a vertebra or for only one of two bone screws to be introduced into the same body in a way that the two bone screws do not occupy the same place.

The starting conditions of the calculation step can comprise values of a starting screw wherein on one side the central axis of this starting screw passes through the centre point of the 2D pedicle traversing surface and on the other side the bone screw insertion surface of the enveloping cylinder of the starting screw is inside the corresponding insertion surface.

In an alternative, the starting point in the pedicle field surfaces beside the insertion point can be chosen to include the most centred portion of screw trajectory inside the 3D traversing surface, e.g. with a least square approach connecting the chosen insertion point/surface of the screw cylinder and the thus defined centre of 3D pedicle traversing surface. According to embodiments disclosed, the calculation step is provided with starting parameters of screw length, screw diameter with the boundary conditions of a predetermined maximum length, and a predetermined maximum diameter, in the geometric model of the target bone.

The steps of the disclosure can be executed on a data processing system comprising means for carrying out the steps of the method claims. The data processing system comprises a computer storage system for the database with the statistical shape model (SSM) and a data storage for the input CT images. These images can be made in advance or just-in-time for the calculation of the screw trajectory. The data processing system usually further comprises input units as keyboards, a mouse or a touch screen/tablet to e.g. choose the vertebra of interest and comprises furthermore output means as display of calculated data of screws and storage for such calculated data.

Further disclosed herein, is a computer program product comprising instructions which, when the program is executed by a computer, cause the computer to carry out the steps of the method according to any one of the embodiments disclosed herein.

Further embodiments of the disclosure are laid down in the dependent claims. Embodiments disclosed herein to provide an efficient method of determining the optimal screw trajectory of the pedicle bone screw maximizing bone density when bone material is replaced by the pedicle bone screw in the morphed vertebra model of the target bone area. This is addressed by the features of claim 10. In particular, a particularly efficient method of determining the optimal screw trajectory comprises:

identifying a space of possible projection planes of the morphed vertebra model using the bone screw insertion surface and pedicle traversing surface;

scanning the space of possible projection planes in order to determine a set of intersection region density projections;

scanning the set of intersection region density projections and calculating corresponding projected bone density scores;

determining the optimum screw trajectory as having a direction normal to the projection plane corresponding to the highest score of the projected bone density score projected bone density scores.

According to a particular embodiment, the length of the bone screw is determined using the three-dimensional geometric model of the target bone area and the optimum screw trajectory, as the distance between the bone screw insertion surface and pedicle traversing surface in the direction of the optimum screw trajectory.

According to a particular embodiment, the step of identifying a space of possible projection planes of the morphed vertebra model comprises: defining a sphere in the morphed vertebra model around a center of the target bone area; defining the space of possible projection planes as a set planes lying normal to the surface of the sphere; and restricting the space of possible projection planes to the set of projection planes with a positive intersection between bone screw insertion surface and pedicle traversing surface.

According to a particular embodiment, the step of scanning of the space of possible projection planes in order to determine a set of intersection region density projections comprises: selecting a number of discretely distributed projection planes within the space of possible projection planes; determining an intersection region of the bone screw insertion surface and pedicle traversing surface for each of the number of discretely distributed projection planes; and summing of all voxels of the morphed vertebra model—representing bone density—within the intersection region and normal to the projection plane to obtain respective intersection region density projections.

According to a particular embodiment scanning the set of intersection region density projections and calculating corresponding projected bone density scores comprises summing of voxels of the intersection region density projection within an area delimited by one or more possible bone screw diameter(s) for each possible position of a bone screw within the corresponding intersection projection, wherein the optimum screw trajectory has an axis crossing the center of the screw diameter corresponding to the highest score of the projected bone density score projected bone density scores.

According to a particular embodiment, in a preparatory step, voxels outside the target bone area are removed/deleted from the morphed vertebra model. The remaining voxels of the morphed vertebra model comprise bone density information related to the target bone area.

According to even further embodiments, in order to improve the performance of the algorithm, the scanning of the space of possible projection planes can be done relatively coarsely in a first iteration. Around the proximity of possible projection planes with the highest projected bone density score, a new set of intersection region density projections are then defined in a narrower space of possible projection planes with even finer resolution at the locations where high scores were found within the previous iteration. This iterative process can be repeated, optionally in combination with an optimization function, resulting in a very efficient method of determining the optimal screw trajectory.

BRIEF DESCRIPTION OF THE DRAWINGS

Preferred embodiments of the disclosure are described in the following with reference to the drawings, which are for the purpose of illustrating the present preferred embodiments of the disclosure and not for the purpose of limiting the same. In the drawings, FIG. 1 shows a flow chart of a method according to an embodiment of the disclosure;

FIG. 5 shows a flowchart of calculating an optimal screw trajectory of the pedicle bone screw, according to a particular embodiment;

DESCRIPTION OF EMBODIMENTS

Figure 2:
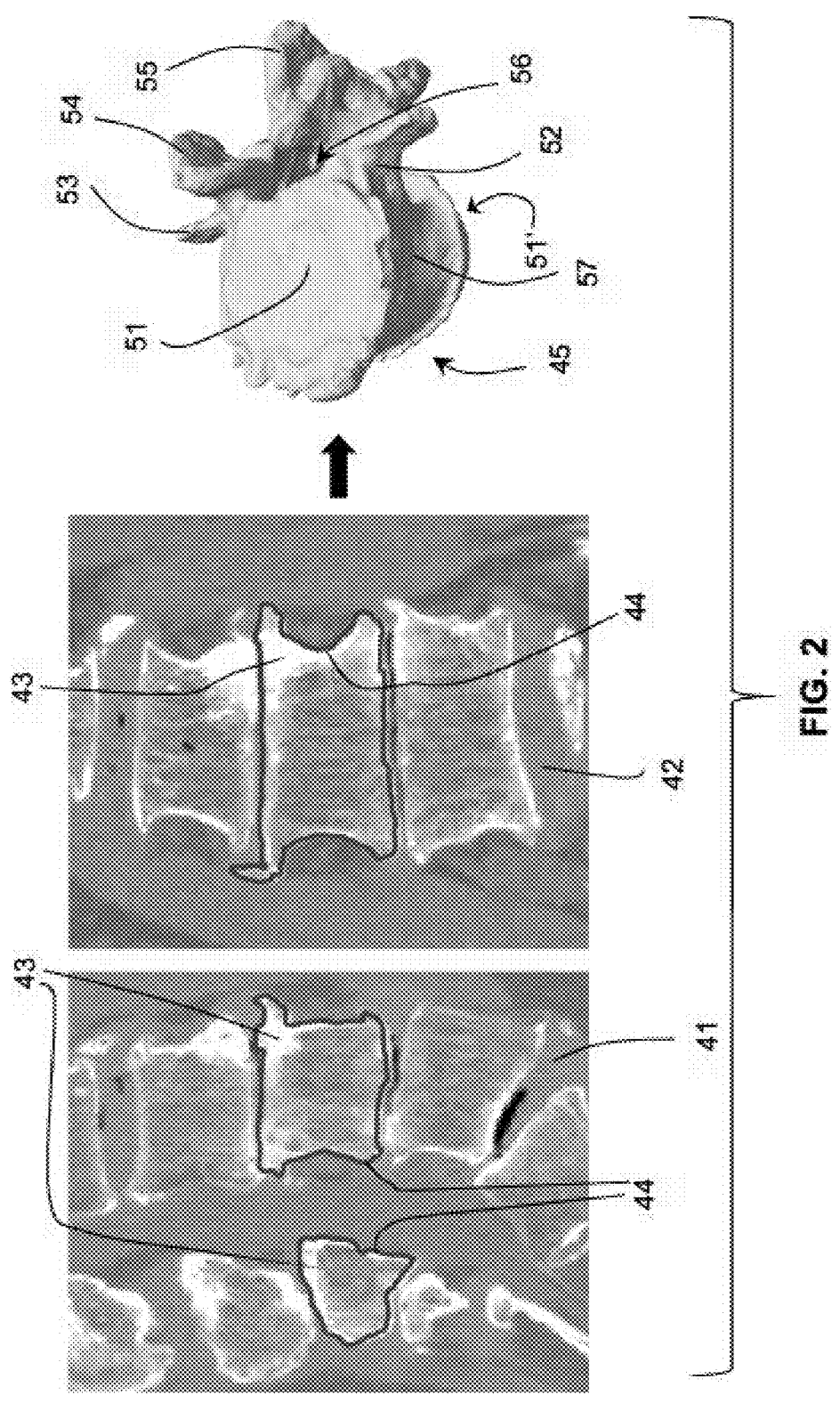
FIG. 2 shows two different CT views with a masked vertebra of interest and a 3D model image representing the CT data relating to the actual bone represented in the model image.

FIG. 1 shows a flow chart of a method according to an embodiment of the disclosure describing a method for determining optimal pedicle screw sizes and orientations for patients in need of spinal fusion. The optimization method requires a data gathering step 1 relating to medical imaging data obtained as 3D computed tomography (CT) composed of discrete voxels. The CT image comprises information allowing to determine bone density information which is extracted and stored for the discrete voxels. The step of obtaining 3D computer tomography data can also be realized by accessing a database, where the prerecorded image is stored. Furthermore, the aim of using 3D computer tomography data is twofold. On one side the data is used as will be explained, to create a data model 45 of the vertebra of interest 43, which is the vertebra into which the pedicle bone screw(s) 60 are to be inserted. On the other side the image data comprises information about bone properties which can be correlated to the space of the discrete voxel. This step of attaching the data to specific voxels can be performed at any time between step 1 and the end of step 7 (see below), i.e. before the start of the optimization calculation.

Loosening of pedicle screws is a clinical complication often related with low bone mineral density. Hence, the optimization of pedicle screw based on patient-specific bone properties can support surgeons in spinal fusion determining.

The following explanation of the flowchart of FIG. 1 is accompanied with reference to the further drawings by reciting reference numerals used in the representation of the vertebra, the related data model 45 and the morphed vertebra model 47.

In a segmenting step 3, the 3D patient image 41, 42 depicting the spinal portion of interest is acquired and segmented to extract 3D geometric models 45 of all the vertebrae 43 that need to be instrumented.

In addition,—in advance—a single statistical shape model, or SSM for short, is provided as step 2 having a predetermined point of bone screw insertion surface 10 and a pedicle traversing surface 20 or voxel plane as a data input for the next handling step of the segmented vertebra image of step 3. According to embodiments disclosed, the SSMs were trained for the different vertebrae using comprehensive dataset of 3D vertebral models. The resulting statistically deformable models of step 2 are able to represent a wide range of vertebral geometries and can be morphed on the segmented patient models 45 of step 3. This morphing step 4 is providing the morphing of the predetermined SSM on 3D geometric model 45 the vertebrae of interest 43 into which the screws are to be implanted creating a morphed vertebra model 47.

On the deformable models from step 2, relevant surfaces 10, 20 and/or 20', 58 are labelled to initialize the optimization process: the pedicle bone screw insertion surface 10, the 3D pedicle traversing surface 20', the 2D pedicle traversing surface 20 and the circumferential contour 58 of the vertebral body between the end plates 51, 51'. The bone screw insertion surface 10 is a surface defined on the SSM (statistical shape model) into which the screw body can enter the vertebra material.

The present method applying a specific morphing step 4 of a template model from step 3 allows the automatic identification of the anatomical surfaces 10, 20, 20', 58 on the vertebral structure. The integration of this method decreases the manual steps needed for the determining, improving its accuracy and robustness.

The morphing step 4 identifies anatomical surfaces on the patient vertebral models 45 from step 3. These points are first used to rigidly place the SSMs at the corresponding spinal level. Further, a point set to image nonrigid registration is performed that morphs the SSMs on the patient's segmented vertebrae 43 in a registration step 5.

These steps 4 and 5 can by explained in connection with FIG. 2 showing two different CT views 41, 42 with a masked vertebra of interest 43 delimited by the respective lines 44 and a 3D model image 45 representing the CT data relating to the actual bone represented in the model image of FIG. 2 which is in fact a data set of voxels. According to embodiments disclosed herein, the method uses more than two different CT views 41, 42 which are shown as example of two CT plans which are here crossing in a right angle in view of a vertical body line.

The 3D model image 45 shows the vertebra of interest 43 with the superior end plate 51, inferior end plate 51', the pedicle 52, the transverse process and coastal facet 53, the superior articular facet 54, the spinous process 55, the vertebral foramen 56 and the body 57. The morphed 3D model 47 is placed in the input CT image model 45 by a coordinate transformation between image and physical coordinate system. The transformation is defined using the voxels properties defined in the information paired with the input CT image 41, 42. The 3D model 45 is used to mask the CT images 41, 42 retaining voxel intensity information, referred to as Hounsfield Unit (HU), within the vertebra of interest 43. Voxel intensity values are converted into bone material properties (Young's modulus):

$$\rho_{app} = 47 + 1.22 * HU \tag{1}$$

$$E_{mod} = 757 * (\rho_{app})^{1.94} \tag{2}$$

After morphing, the contour 59 of the labelled endplates 51, 51' from step 3 allow the automatic identification of the patient's pedicle regions. A homogeneous grid within the pedicle regions is created using a region growing method in radial direction from the endplate 51, 51' centres. A polar coordinate system is defined on the superior endplate 51 of the vertebral model. In an alternative, the inferior end plate 51' is used for it. The points defining the endplate boundary 59 are moved by increasing their radial components 8 with consistent steps all around the vertebral endplate 51 or 51'. For each radial increase, a homogeneous grid is generated in

Figure 4B:
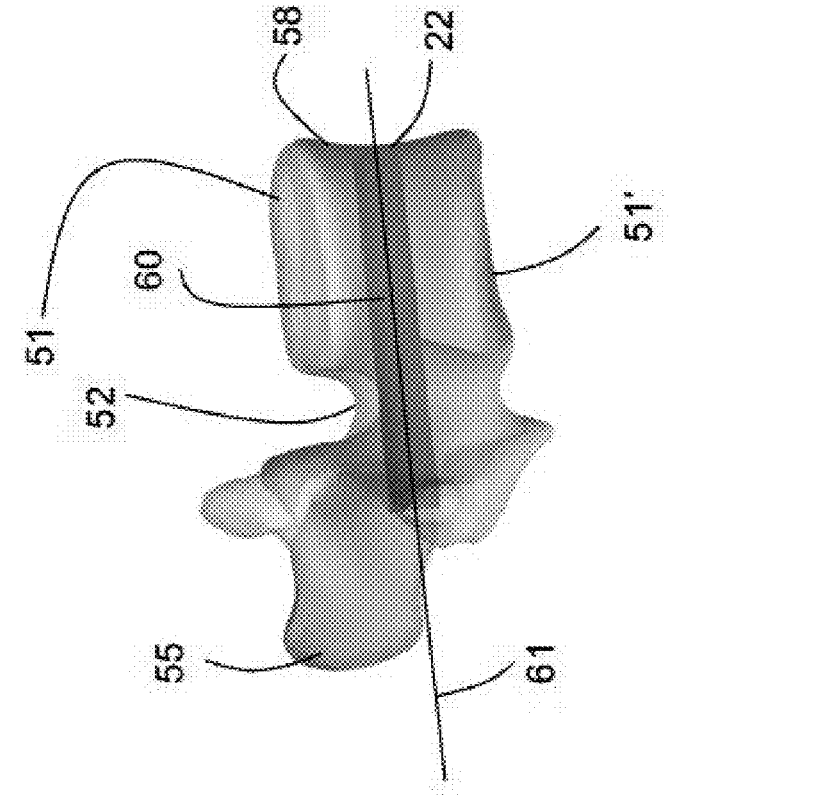
FIG. 4B shows a schematic perspective view from the side on the vertebra shown in FIG. 4A.
Figure 4A:
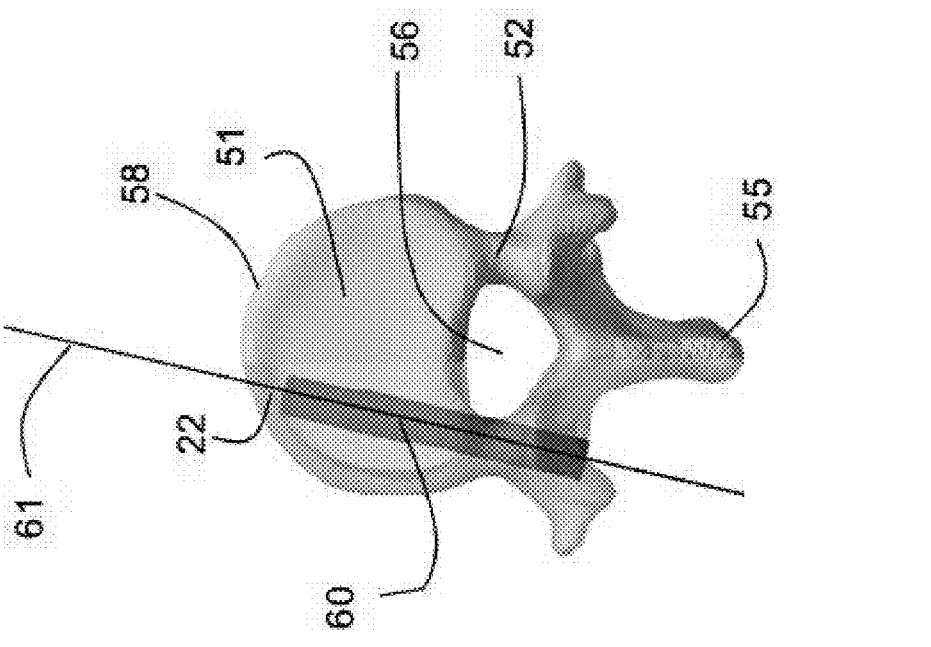
FIG. 4A shows a schematic perspective view from above on the vertebra of interest with one screw inserted in a configuration provided according to the disclosure.
Figure 6:
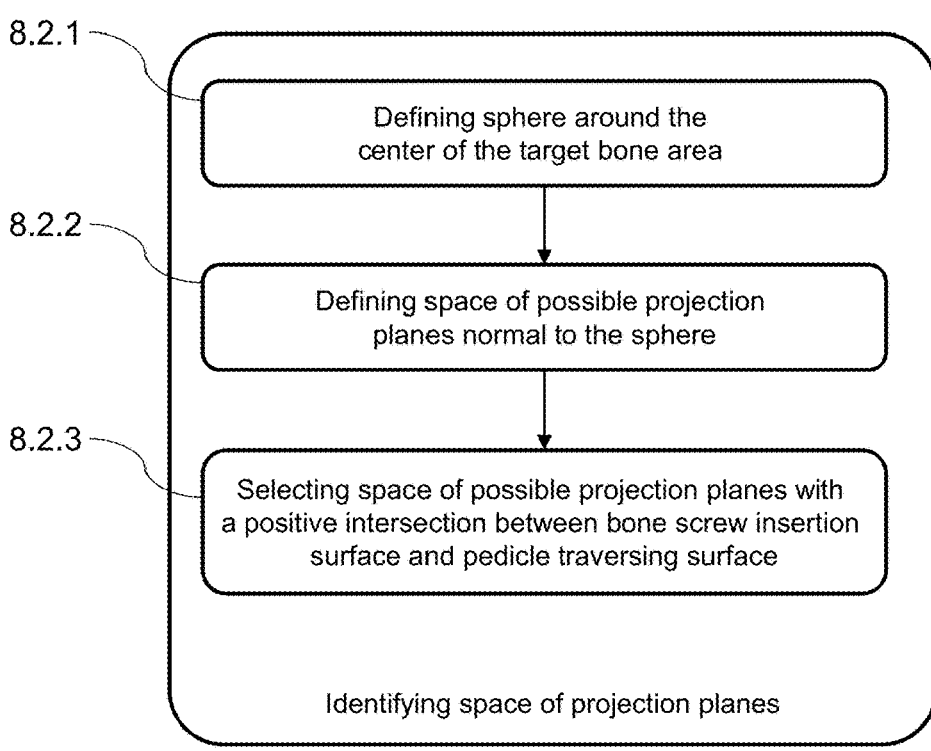
FIG. 6 shows a flowchart of substeps of identifying a space of possible projection planes, according to a particular embodiment.
Figure 7:
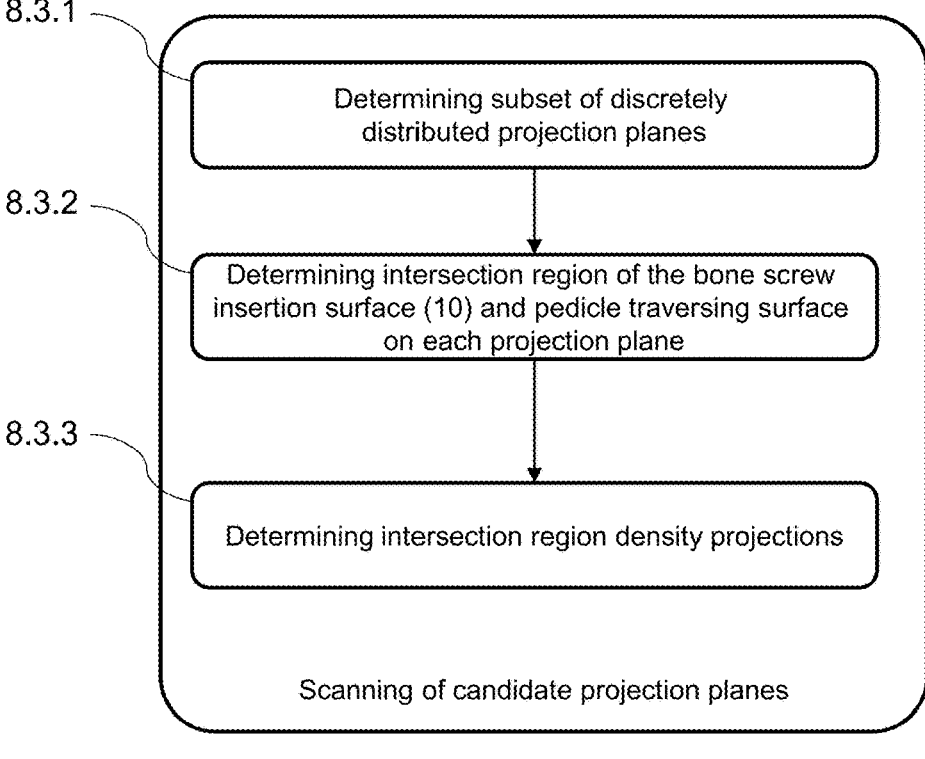
FIG. 7 shows a flowchart of substeps of scanning the possible projection planes, according to a particular embodiment.
Figure 8:
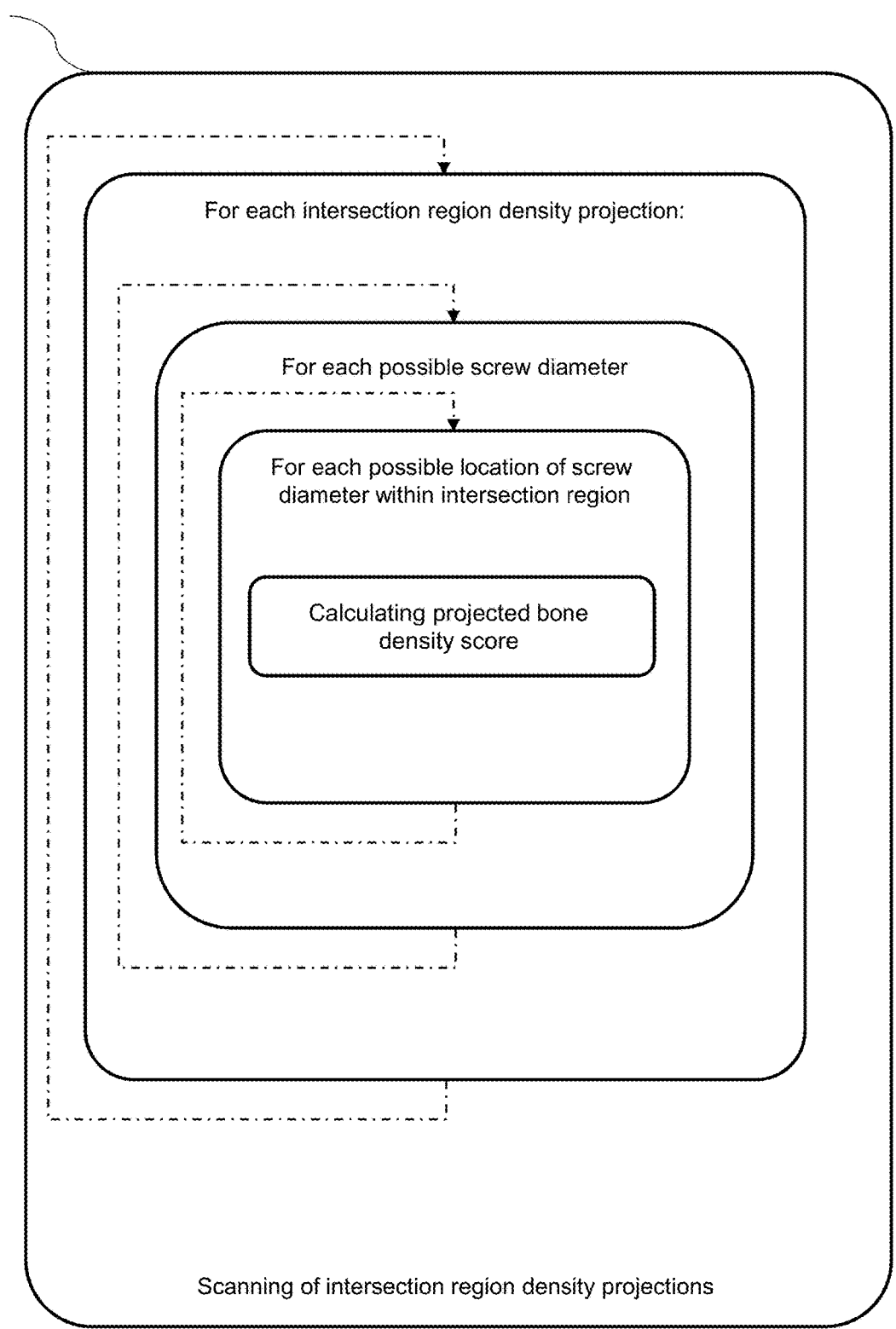
FIG. 8 shows a flowchart of scanning of intersection region density projections, according to a particular embodiment.
Figure 9:
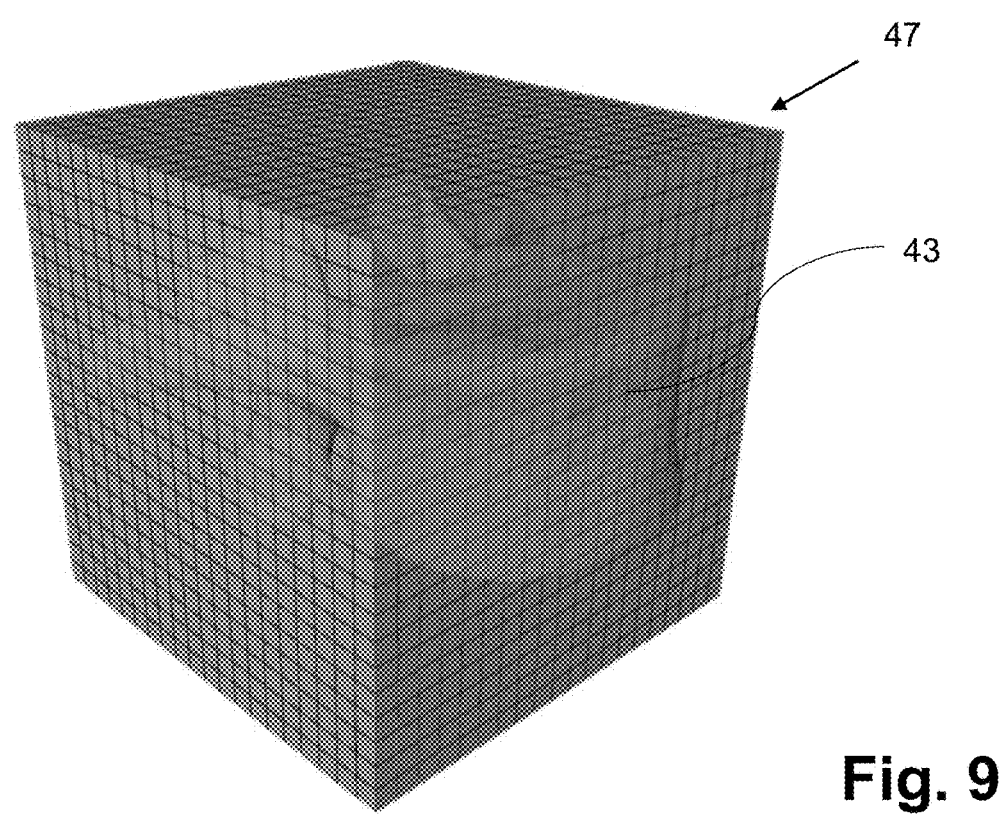
FIG. 9 shows a schematic perspective view of voxels of a morphed vertebra model.
Figure 10:
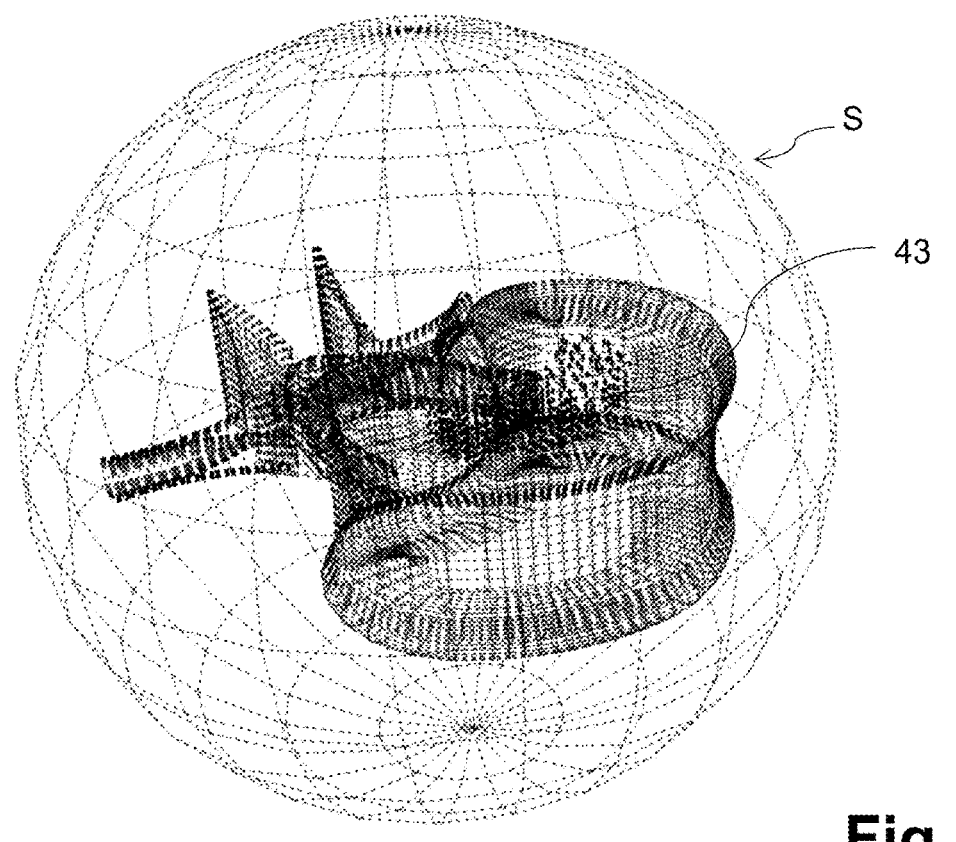
FIG. 10 shows a perspective view of nodes defined on the surface of the sphere (centered around the target bone area) at the intersections of lines of longitude respectively latitude of the sphere.
Figures 11A, 11B, 11C:
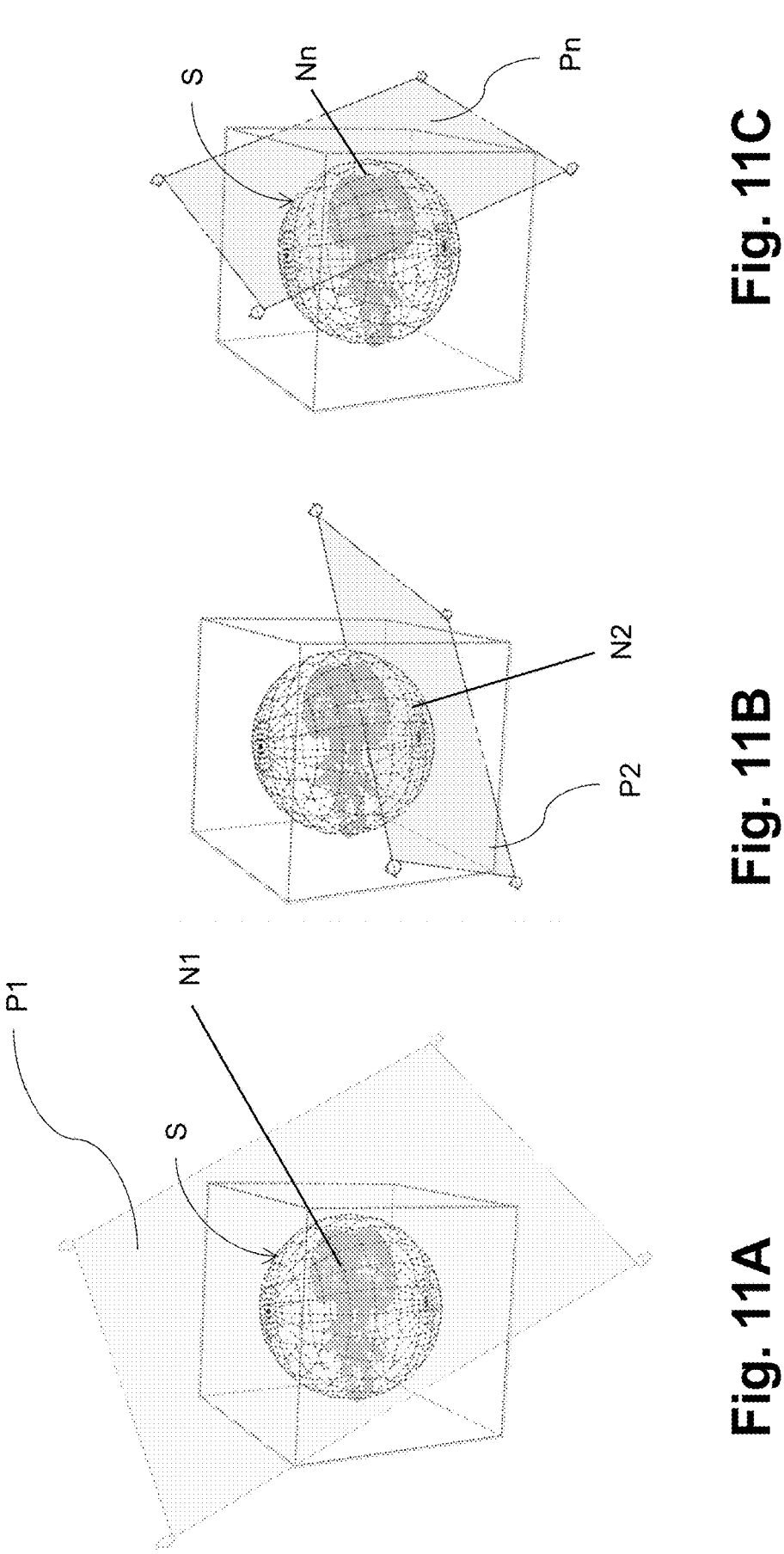
FIG. 11A-11C show a sequence of schematic perspective views of possible projection planes of the morphed vertebra model normal to a sphere centered around the target bone area.
Figure 12A:
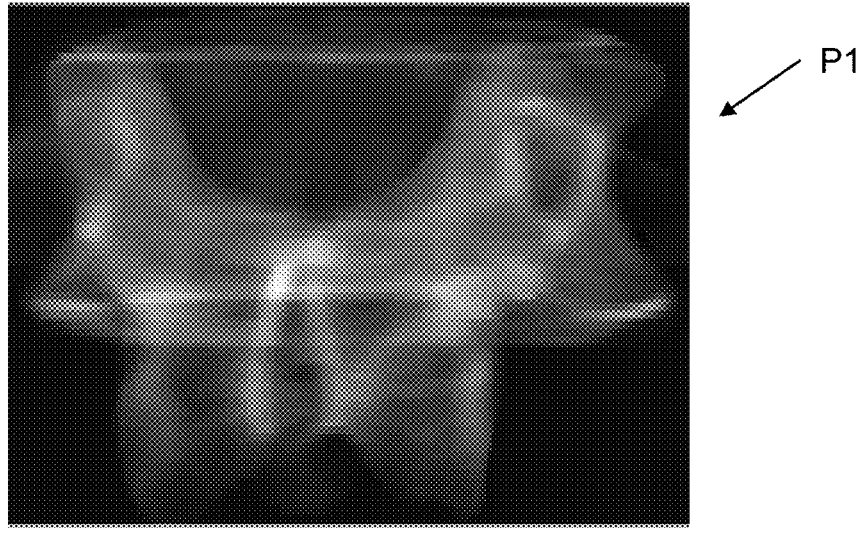
FIG. 12A shows a projection plane of the morphed vertebra model.
Figure 12B:
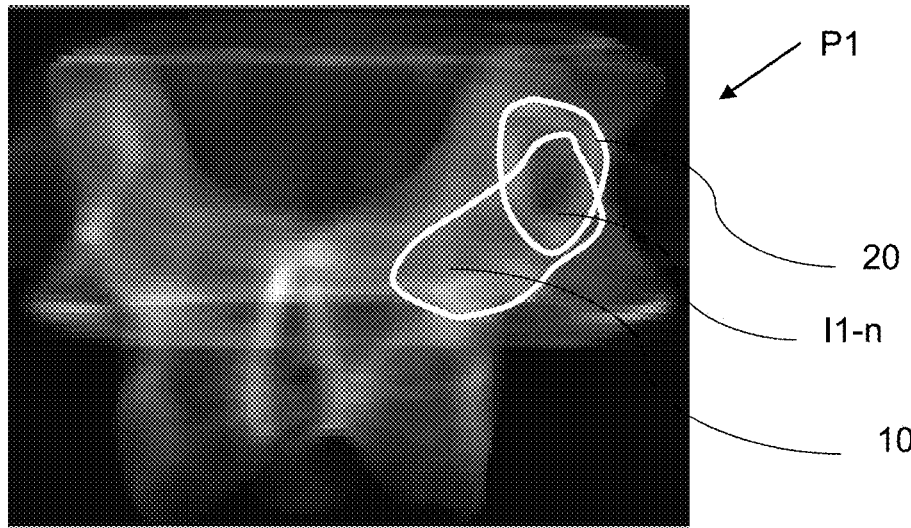
FIG. 12B shows the projection plane of the morphed vertebra model of FIG. 12A with the bone screw insertion surface and pedicle traversing surface marked.
Figure 12C:
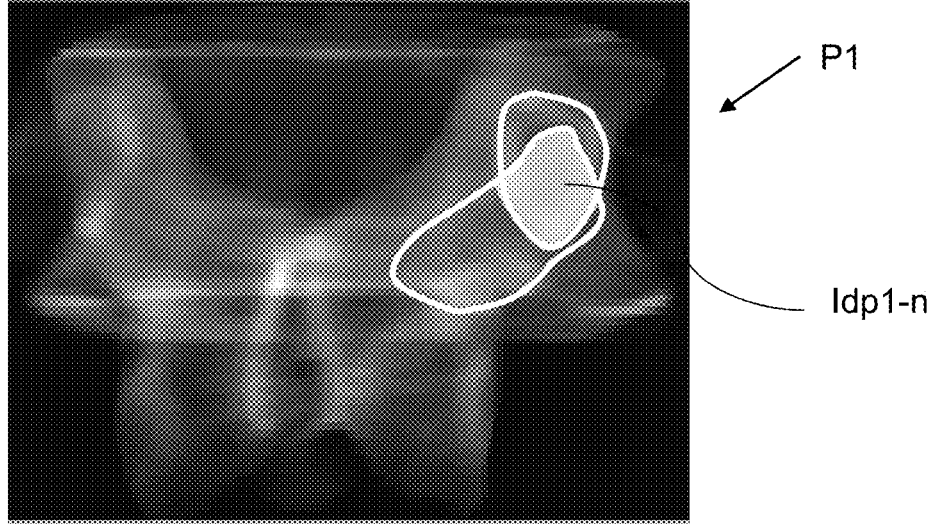
FIG. 12C shows the projection plane of the morphed vertebra model of FIGS. 12A and 12B, identifying an intersection region of the bone screw insertion surface and pedicle traversing surface.
Figure 12D:
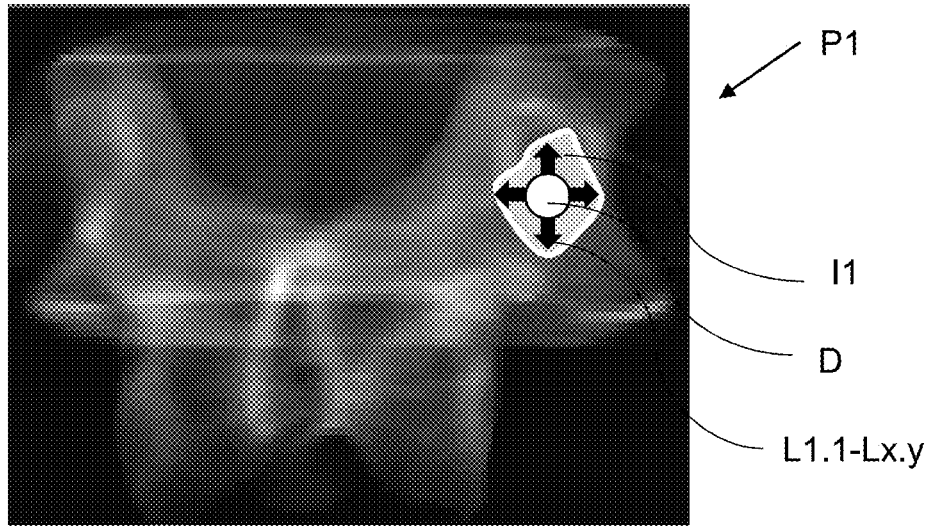
FIG. 12D shows the projection plane of the morphed vertebra model of FIGS. 12A, 12B and 12C illustrating the scanning of possible positioning of pedicle screw with a possible diameter within an intersection region density projection.

8 the axial direction of the vertebra 43, resulting in 2D surfaces that are added around the endplate 51, 51' perpendicularly to the radial direction. A volumetric grid is generated all around the vertebral body 57, and since the pedicles 52 are the only structures that extend from its side, the points of volumetric grid that lie inside the vertebral 3D model represent points inside the pedicle regions. Additionally, points inside the pedicle 52 have to be selected with a threshold value of perpendicular distance to the vertebral boundary. Such a threshold value can be chosen to be at least 1 mm or 2.5 mm as selected minimum safety distance 21, which minimum safety distance 21 avoids the pedicle bone screw 60 (see FIG. 4A) to break through the pedicle wall. In the drawings, reference numeral 21 is used for showing the distance between the 3D pedicle traversing surface 20' or the 2D pedicle traversing surface 20 and the pedicle wall surface. The resolution of the grid depends on the one of the input CT images to include all the voxel information in the optimization.

The above determination of the 3D pedicle traversing surface 20' and the 2D pedicle traversing surface 20 is based on the end plate 51, 51'. In an alternative approach, the sagittal plane 35 can be used, easily identifiable by the spinous facet 55 and a centre line through the end plate 51, 51'. In a further alternative, the vertebral foramen 56 can be identified and used to determine the pedicles 52 with the 2D pedicle traversing surface 20 being the smallest diameter portion of bone material.

Within the 3D homogeneous grid of the 3D pedicle traversing surface 20' that depicts the pedicle region, a 2D pedicle traversing surface 20 can be determined at the overall minimum transverse pedicle width. A point on this 2D pedicle traversing surface 20 together with a point in the bone screw insertion surface 10 define the screw trajectory 61 of the pedicle screw 60. The contour 59 of the body 57 around the end plates 51, 51' comprises a body side surface 58. As further safety distance, a minimum safety distance 22 from this body side surface 58 is taken into account, mainly limiting the length of the screw. These safety distances ensure that the pedicle bone screw 60 does not perforate the vertebral wall.

Figures 3A, 3B, 3C:
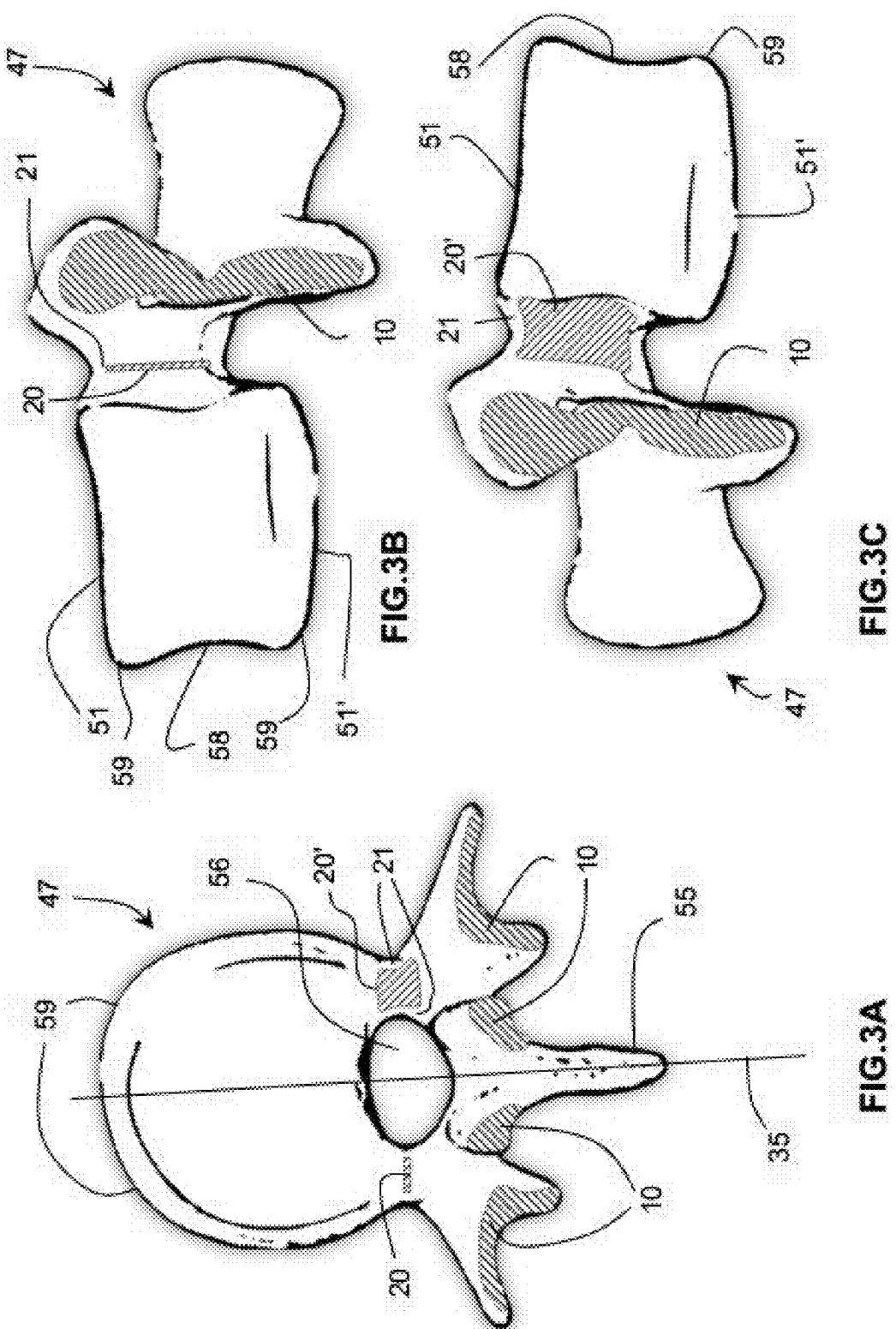
FIG. 3A shows a schematic view from above on the vertebra of interest reflecting two embodiments on the different sides of the sagittal plane.
FIG. 3B shows a side view from the left side of FIG. 3A with insertion and pedicle surfaces according to said embodiments of the disclosure.
FIG. 3C shows a side view from the right side of FIG. 3A with insertion and pedicle surfaces according to said embodiments of the disclosure.

Additionally, besides the body side surface 58, the sagittal plane 35 provides a further boundary plane for the pedicle screw 60, when as usually two pedicle bone screws 60 are placed through both pedicles 52, since the two pedicle bone screws 60 should not interfere in the placement of the other. It is possible to provide solutions (screw trajectory) for one pedicle bone screw 60 not regarding this boundary condition and combine it with a solution for the other screw checking, if the solutions are compatible, i.e. are not being calculated to take the same space. The bone screw insertion surfaces from step 3 are morphed on the patient vertebrae 43 together with the SSMs. The bone screw insertion surfaces 10 as well as the 3D and 2D pedicle traversing surfaces 20' and 20, respectively, both at the inside the pedicle, are shown as hatched in FIGS. 3A, 3B and 3C on the morphed model 47. It is noted that the representation of the morphed 3D model is as such not complete, since it also comprises, at least before the calculation step, the information about the bone property especially the bone density.

The insertion 10 and pedicle traversing surfaces 20, 20', together with the bone edges, especially side surface 58, from the morphed 3D models from step 4 define the optimization space. A combination of insertion surface 10 and pedicle traversing surface 20 points from the grids defines the screw trajectory 61.

The input parameters for the optimization are the insertion point on the bone screw insertion surface 10, the pedicle point, i.e. the centre of the screw in the grid area of the 2D pedicle traversing surface 20, the screw diameter, and the screw length, optionally deducted from the surface distance 22 in view of the body side surface 58, all of which are optimized avoiding perforation of the bone structure using the morphed vertebra models 47 from step 4. According to embodiments disclosed, the insertion point is chosen around the centre of the surface delimited as bone screw insertion surface 10. The insertion point as such is not a point but the section of the 3D surface of the usually not flat vertebra surface with the cylindrical model surface of the screw body and is in fact a 3D surface. It is mentioned above that the starting point in the 2D pedicle traversing surface 20 can be chosen as centre of the 2D pedicle traversing surface 20, thus defining the screw trajectory 61. In other embodiments, the starting point in the pedicle traversing surfaces 20, 20' beside the insertion point can be chosen to include the most centred portion of screw trajectory 61 inside the 3D pedicle traversing surface 20', e.g. with a least square approach connecting the chosen insertion and the thus defined "centre" of 3D pedicle traversing surface 20'.

Step 8 comprises an iterative calculation implemented to compare combinations of the input parameters (the bone screw insertion surface 10, the pedicle point, i.e. the centre of the screw in the grid area of the 2D pedicle traversing surface 20, the screw diameter, and the screw length) and extract the optimal solution, which can be a genetic calculation approach based on parameters as sample size in each iteration, percentage of mutation, percentage of best cases passed to next iteration, etc. as known by persons skilled in the art. It is also possible to provide a limited number of optimum or near optimum solutions in view of a choice for the surgeon. A cylinder simplifying (approximating) a pedicle bone screw 60 is created using a combination of the input parameters and placed in the 3D morphed vertebral 47 model along a predetermined screw trajectory 61. First, the calculation excludes cylinders that are perforating the morphed vertebra model 47 from step 4. If the screw is not perforating, the cylinder is placed in the 3D image mask from step 5 using the coordinate transformation between the CT image 41, 42 and physical coordinate systems. The image voxels containing bone material properties values are extracted within the screw volume and used for the computation of the bone material distribution within the cylinder.

To initialize the optimization method, a random population of parameters' combinations is created. Each combination is tested using the bone density computation. After testing, random changes and recombination of the parameters are introduced to create the population for the next iteration. The population in the last iteration contains the best performing parameters' combinations.

The distribution of bone material properties is defined as the performance of each parameters' combination, thus used to optimize the final solution. The optimal screw trajectory and screw dimension resulting from the optimization are the one maximizing the voxel-based bone material properties within the screw volume which is the output of step 9. As mentioned above, the output can also comprise a number of optimum or near-optimum solutions which may have different advantages of handling, screw head connections between different screws etc.

Turning now to FIGS. 5 to 12, a particularly efficient embodiment of calculating an optimal screw trajectory 61 of the pedicle bone screw 60 (Step 8) shall be described.

FIG. 5 shows a flowchart of steps 8.1 to 8.6 of calculating an optimal screw trajectory 61 of the pedicle bone screw.

In a first, preparatory step 8.1, voxels outside the target bone area 43 (shown on FIG. 9 with dark grey) are removed/deleted from the morphed vertebra model 47. The remaining voxels of the morphed vertebra model 47 (shown on FIG. 9 with light grey) comprise bone density information related to the target bone area 43.

According to further embodiments, the voxel mesh of the morphed vertebra model 47 is downsampled in order to improve the performance of the calculation.

In a second step 8.2, a space of possible projection planes of the morphed vertebra model 47 is identified using the bone screw insertion surface 10 and pedicle traversing surface 20. Details of substep 8.2 shall be described with reference to FIG. 6, which shows a flowchart of substeps 8.2.1 to 8.2.3 of the step of identifying a space of possible projection planes, according to a particular embodiment. In substep 8.2.1, a sphere S is defined in the morphed vertebra model 47 around a center of the target bone area 43 (see FIG. 10). In a substep 8.2.2, the space of possible projection planes is determined, the possible projection planes lying normal to the surface of the sphere S. The space of possible projection planes (as shown on FIGS. 11A to 11C, including non-feasible projection planes) is delimited in a step 8.2.3 in such a way that only projection planes with a positive intersection between bone screw insertion surface 10 and pedicle traversing surface 20 remain, the projections being normal to the projection plane, thereby obtaining the space of possible projection planes.

In a third step 8.3, the space of possible projection planes is scanned in order to determine a set of intersection region density projections Idp1-$n$. Details of substep 8.3 shall be described with reference to FIG. 7, which shows a flowchart of substeps 8.3.1 to 8.3.3 of step 8.3 of scanning the possible projection planes. In a first substep 8.3.1, a subset of discretely distributed projection planes P1-$n$ is obtained from the space of possible projection planes. According to a particular embodiment, as illustrated on FIG. 10, nodes are defined on the surface of the sphere P at the intersections of lines of longitude respectively latitude of the sphere as shown on the sequence of FIGS. 11A to 11C. The lines of longitude respectively latitude of the sphere are spaced equidistantly according to a defined resolution. The discretely distributed projection planes P1-$n$ are arranged normal to the sphere S at said nodes, but within the space of positive intersections delimited in a step 8.2.3. In subsequent substep 8.3.2, as depicted on the sequence of FIGS. 12A to 12C, on each projection plane P1-$n$ of the subset of discretely distributed projection planes P1-$n$, an intersection region I1-$n$ of the bone screw insertion surface 10 and pedicle traversing surface 20 is determined, the obtained intersection region I1-$n$ defining the space of possible screw trajectories. Thereafter, in substep 8.3.3 all voxels of the morphed vertebra model 47 (representing bone density) within the intersection region I1-$n$ and normal to the projection plane P1-$n$ are summed to obtain a respective intersection region density projection Idp1-$n$ for each of the discretely distributed projection planes P1-$n$. The voxels of the intersection region density projection Idp1-$n$ each define the sum of all bone densities projected on the respective projection plane P1-$n$. According to embodiments disclosed herein, the Hounsfield Unit (HU) values of the CT image are used either directly or after being converted into bone material properties according to Young's modulus for obtaining the intersection region density projections Idp1-$n$.

In a fourth step 8.4, each intersection region density projection Idp1-*n* is scanned with the possible bone screw diameters D1-*n* and/or possible location L1.1-*x.y* within the intersection projection I1-*n*. Details of substep 8.4 shall be described with reference to FIG. 8. In a first, iterative substep, for each intersection projection I1-*n*, the voxels of the intersection region density projection Idp1-*n* within an area delimited by a possible bone screw diameter D1-*m* are summed. This is repeated for each possible bone screw diameter D1-*m* and each possible location L1.1-*x.y* of the respective bone screw diameter D1-*m* within the respective intersection region I1-*n* to obtain a respective projected bone density score Pbds1.1.1.1-Pdbs n.m.x.y. The scanning of an intersection region I1 is illustrated on FIG. 12D with black block arrows illustrating the scanning of possible locations P1.1.*x.y* of a particular screw diameter D1-*m* within the respective intersection region I1.

Thereafter, in step 8.5, the optimum screw trajectory is determined as having a direction normal to the projection plane P1-*n* respectively an axis crossing the center of the screw diameter D1-*m* corresponding to the highest projected bone density score PbdsMAX.

Having determined the optimum screw trajectory, in a step S8.6, the bone screw length is determined using the three-dimensional geometric model 45 of the target bone area 43 and the optimum screw trajectory, in particular as the distance between the bone screw insertion surface 10 and pedicle traversing surface 20 in the direction of the optimum screw trajectory.

According to further embodiments, as illustrated on FIG. 5 with a dashed arrow, the process of scanning possible projection planes and the scanning of intersection density projections (steps 8.3 and 8.4) is an iterative process. In order to improve the performance of the algorithm, the incremental scanning of the projection planes (step 3) can be done relatively coarsely in a first iteration. In particular, the resolution—of the lines of longitude respectively defining the nodes where the discretely distributed projection planes P1-*n* are defined—is lower.

In subsequent iterations, new projection planes are defined around the proximity (angular proximity on the sphere spanned around the center of the target bone area) of possible projection plane(s) with the highest projected bone density score(s) Pbds (computed in step 4). In particular, a new subset of discretely distributed projection planes is determined around the proximity of possible projection plane(s) with the highest projected bone density score(s) Pbds with a resolution increased as compared to the previous iteration(s). The steps 8.3.2, 8.3.3 and 8.4 are carried out again using the new subset of discretely distributed projection planes P1-*n*.

This iterative process (steps 8.3 and 8.4) is repeated for a defined number of iterations. Alternatively, or additionally, the iterative process is repeated until the highest projected bone density score PbdsMAX of the current iteration is equal to the highest projected bone density score PbdsMAX of the previous iteration or exceeds the highest projected bone density score PbdsMAX of the previous iteration by no more than a threshold improvement margin. Optionally the iterative process is combined with an optimization function, resulting in a very efficient method of determining the optimal screw trajectory.

Finally, after the iterative process (steps 8.3 and 8.4) is finished, the in step 8.5, the optimum screw trajectory is determined as having a direction normal to the projection plane P1.*n* respectively an axis crossing the center of the screw diameter D1-*m* corresponding to the highest projected bone density score projected bone density score PbdsMAX of any iterations.

LIST OF REFERENCE SIGNS

1 data gathering step
2 segmenting step
3 providing a statistical shape model
4 morphing step
5 masking and registration step
6 determination of parameters from the morphed model
7 determination of boundary conditions
8 optimization calculation
9 output step
10 bone screw insertion surface
20 2D pedicle traversing surface
20' 3D pedicle traversing surface
21 minimum safety distance (pedicle)
22 minimum safety distance (body)
35 sagittal plane
41 first CT view
42 second CT view
43 vertebra of interest
44 delimitation line
45 3D geometric model, i.e. data model representation of vertebra of interest, in short: vertebra model
47 morphed vertebra model
51 superior end plate
51' inferior end plate
52 pedicle
53 transverse process and coastal facet
54 superior articular facet
55 spinous facet
56 vertebral foramen
57 body
58 body side surface
59 contour of end plate
60 pedicle bone screw
61 screw trajectory
P1-*n* projection planes
N1-*n* normals to the projection planes P1-*n*
S sphere (centered around the target bone area)
I1-*n* intersection regions
Idp1-*n* intersection region density projections
D1-*m* possible screw diameters
Pbds1.1.1.1-*n.m.x.y* projected bone density scores
PbdsMAX highest projected bone density score

The invention claimed is:

1. A method for determining an optimal screw trajectory of a pedicle bone screw comprising the following steps:

obtaining a computed tomography (CT) image of a target bone area intended to receive the pedicle bone screw;

establishing an individualized three-dimensional geometric model of the target bone area based on the CT image, the individualized three-dimensional geometric model including bone density information;

accessing a database comprising a three-dimensional bone area model, wherein the three-dimensional bone area model comprises a bone screw insertion surface and a pedicle traversing surface;

morphing the three-dimensional bone area model to the individualized three-dimensional geometric model of the target bone area generating a morphed vertebra model comprising the bone screw insertion surface and the pedicle traversing surface of the three-dimensional bone area model as well as the bone density information of the individualized three-dimensional geometric model, wherein the morphing comprises transferring the bone screw insertion surface and the pedicle traversing surface onto the individualized three-dimensional geometric model;

calculating an optimal screw trajectory of the pedicle bone screw maximizing bone density when bone material is replaced by the pedicle bone screw in the morphed vertebra model of the target bone area; and outputting the optimal screw trajectory for the pedicle bone screw in the morphed vertebra model of the target bone area.

2. The method according to claim 1, further comprising outputting a length and diameter of the pedicle bone screw.

3. The method according to claim 2, wherein a first threshold value as length safety distance is provided within the determination of a screw length based on a body side surface of a body of the target bone area.

4. The method according to claim 1, wherein the morphing of the three-dimensional bone area model to the individualized three-dimensional geometric model comprises providing a three-dimensional pedicle traversing surface within the morphed vertebra model of the target bone, the three-dimensional pedicle traversing surface being modelled in the three-dimensional bone area model within the database and morphed with the individualized three-dimensional geometric model.

5. The method according to claim 4, wherein the morphing of the three-dimensional bone area model further comprises providing a two-dimensional pedicle traversing surface, wherein the two-dimensional pedicle traversing surface as the pedicle traversing surface is based on the three-dimensional pedicle traversing surface and corresponds to a plane of minimum transverse pedicle width in a pedicle.

6. The method according to claim 5, wherein a first threshold value as contour safety distance is provided within the determination of the two-dimensional pedicle traversing surface-, generated as a three-dimensional curve inside an outer edge of the pedicle, delimiting voxels used in the three-dimensional pedicle traversing surface and subsequently the two-dimensional pedicle traversing surface.

7. The method according to claim 5, wherein starting conditions of the step of calculating an optimal screw trajectory of the pedicle bone screw comprise values of a starting screw wherein the central axis of the starting screw passes through a centre point of the two-dimensional pedicle traversing surface, wherein the bone screw insertion surface of an enveloping cylinder of the starting screw is inside the bone screw insertion surface.

8. The method according to claim 4, wherein starting conditions of the step of calculating an optimal screw trajectory comprise values of a starting screw wherein the central axis of the starting screw is chosen to be the most centred portion of axis inside the three-dimensional pedicle traversing surface.

9. The method according to claim 1, wherein the step of calculating an optimal screw trajectory comprises:

creating a cylinder approximating the pedicle bone screw and placing the cylinder in the morphed vertebra model along an initial screw axis calculated based on the bone screw insertion surface and the pedicle traversing surface; and calculating bone material density within the cylinder approximating the pedicle bone screw in the morphed vertebra model.

10. The method according to claim 9, further comprising:

excluding cylinders approximating the pedicle bone screw that are perforating the morphed vertebra model; and using bone material properties within the cylinder approximating the pedicle bone screw, extracted from image voxels in the morphed vertebra model.

11. The method according to claim 1, wherein the step of calculating an optimal screw trajectory of the pedicle bone screw comprises:

identifying a space of possible projection planes of the morphed vertebra model using the bone screw insertion surface and pedicle traversing surface;

scanning possible projection planes in order to determine a set of intersection region density projections;

scanning the set of intersection region density projections and calculating corresponding projected bone density scores; and determining the optimum screw trajectory as having a direction normal to the projection plane corresponding to a highest score of the projected bone density scores.

12. The method according to claim 11, further comprising determining the length of the pedicle bone screw using the individualized three-dimensional geometric model of the target bone area and the optimum screw trajectory, as the distance between the bone screw insertion surface and pedicle traversing surface in the direction of the optimum screw trajectory.

13. The method according to claim 11, wherein the step of identifying possible projection planes of the morphed vertebra model comprises:

defining a sphere in the morphed vertebra model around a center of the target bone area;

defining the possible projection planes as a set planes lying normal to the surface of the sphere; and restricting the possible projection planes to the set of projection planes with a positive intersection between bone screw insertion surface and pedicle traversing surface.

14. The method according to claim 11, wherein the step of scanning of possible projection planes comprises:

selecting a number of discretely distributed projection planes within the possible projection planes;

determining an intersection region of the bone screw insertion surface and pedicle traversing surface for each of the number of discretely distributed projection planes; and summing of all voxels of the morphed vertebra model representing bone density within the intersection region and normal to the projection plane to obtain respective intersection region density projections.

15. The method according to claim 11, wherein scanning the set of intersection region density projections and calculating corresponding projected bone density scores comprises summing of voxels of the intersection region density projection within an area delimited by one or more possible bone screw diameter for each possible position of a bone screw within the corresponding intersection projection, wherein the optimum screw trajectory has an axis crossing the center of the screw diameter corresponding to the highest score of the projected bone density scores.

16. The method according to claim 1, wherein the calculating step is provided with starting parameters of screw length, screw diameter with boundary conditions of a predetermined maximum length, and a predetermined maximum diameter, in the individualized three-dimensional geometric model of the target bone area.

17. The method according to claim 1, wherein the morphing of the three-dimensional bone area model comprises providing a sagittal plane within the geometric morphed vertebra model to determine the pedicle traversing surface.

18. The method according to claim 17, wherein the sagittal plane of a body of the target bone area provides a first threshold value which the contour and the tip of the pedicle bone screw has not to pass for any one pedicle bone screw to be introduced into a same body or for only one of two pedicle bone screws to be introduced into the same body in a way that the two pedicle bone screws do not occupy the same place.

19. The method according to claim 1, wherein the morphing of the three-dimensional bone area model comprises determining a vertebral foramen within the geometric morphed vertebra model to determine the pedicle traversing surface as smallest bone material diameter on sides of the vertebral foramen.

20. The method according to claim 1, wherein the step of calculating an optimal screw trajectory of the pedicle bone screw is repeated iteratively for maximizing bone density when bone material is replaced by the pedicle bone screw in the morphed vertebra model of the target bone area.

\* \* \* \* \*